United States Patent

Adachi

[11] Patent Number: 5,885,233
[45] Date of Patent: Mar. 23, 1999

[54] MASSAGE DEVICE

[75] Inventor: Kazunobu Adachi, Chiba, Japan

[73] Assignee: Baron & Co., Ltd., Ichikawa, Japan

[21] Appl. No.: 647,806

[22] Filed: May 15, 1996

[30] Foreign Application Priority Data

May 17, 1995 [JP] Japan .................................... 7-118721

[51] Int. Cl.$^6$ .............................. A61H 7/00; A61H 19/00
[52] U.S. Cl. ........................... 601/138; 601/136; 600/38; 600/41; 604/349; 604/385.1
[58] Field of Search .................................... 601/138, 136, 601/137; 600/38, 41, 39; 128/842, 861, 844, 918; 604/349, 385.1

[56] References Cited

U.S. PATENT DOCUMENTS

| | | | |
|---|---|---|---|
| 4,320,752 | 3/1982 | Comparetto | 604/349 |
| 4,781,709 | 11/1988 | Grubman | 128/844 |
| 4,869,723 | 9/1989 | Harmon | 604/349 |
| 5,112,324 | 5/1992 | Wallace | 604/349 |
| 5,538,584 | 7/1996 | Metz | 128/844 |
| 5,620,429 | 4/1997 | Al-Saleh | 600/41 |

*Primary Examiner*—Richard J. Apley
*Assistant Examiner*—Justine R. Yu
*Attorney, Agent, or Firm*—Notaro & Michalos P.C.

[57] ABSTRACT

An axial elongated main body of a container with flexible material has a filler member of soft and more resilient material filled and fixed in the main body of the container. A penis insertion part is arranged at a substantial central part of the filler member and lubricant agent is coated at the penis insertion part. The penis insertion part has a narrow insertion part and a slack insertion part. The narrow insertion part is provided with a plurality of projections. The massage device so constructed is operated such that a lid, if this is set at the device, is taken off of the device and if the lid is not set at the device, a packaging bag is broken and then lubricant agent is coated on the penis insertion part. Or if the device is coated in advance with lubricant agent, the device may be used as it is.

9 Claims, 6 Drawing Sheets

MASSAGE DEVICE

BACKGROUND OF THE INVENTION

1. Field of the Invention

This invention relates to a massage device which is preferable in use to apply a massage to male sexual organs.

2. Description of the Related Art

Although in the prior art, there have been well known to provide various kinds of devices or tools for applying a massage to male sexual organs, they are expensive and show an outer appearance to cause its object to be easily recognized at a glance, a shamed feeling is generated at a purchaser on purchasing the device or the device can be bought at a specific site, and so a sufficient distribution of the device is not yet attained.

To the contrary, it has been well requested, on one hand, to provide means for satisfying physical requirements of a male conveniently and safely so as to prevent Aids caused by sexual intercourse with non-specified many persons or to prohibit sexual crimes, and on the other hand, to provide a convenient high performance massage device capable of taking sperms in order to perform a study or treatment with development of modern medical system, and taking and keeping sperms for artificial fertilization for the sake of an accident of a husband or a couple having no child.

SUMMARY OF THE INVENTION

In view of the foregoing, it is an object of the present invention to provide a less-expensive, convenient, high performance, convenient-in-use and safe massage device for male sexual organs.

In order to accomplish the aforesaid object, according to one aspect of the present invention, there is provided a massage device comprised of an axial elongated main body of a container with flexible material; a filler member of soft and resilient material filled and fixed in the main body of the container; a penis insertion part arranged axially at a substantial central portion of the filler member; and lubricant agent coated in the penis insertion part, wherein the penis insertion part has a narrow insertion part and a slack insertion part arranged in subsequent to the narrow insertion part, the narrow insertion part is provided with a plurality of projections formed by various slits.

The massage device constructed as above is operated such that if the device has a lid, the lid is taken and if the device has no lid, the packaging bag is broken, the penis insertion part is coated with the lubricant agent. Or if the device is coated with the lubricant agent in advance, the device may be used as it is. Then, the main body of the container is held with a hand and erect male sexual organs are inserted into the penis insertion part as described later and then a sperm emission operation is carried out.

At that time, the penis insertion part constructed by the filler member of soft and more resilient material quality and the lubricant agent coated on the penis insertion part may promote a smooth sperm emission operation without damaging the sponge body or skin of the male sexual organs. A more comfortable stimulation and a fast sperm emission operation can be given to a user of the device by a suitable fastening of the device with a hand through the main body of the container as well as a press contact with the sexual organs by the projections.

In the case that a condom is used, sperm liquid is accumulated in the condom and in turn in the case that no condom is used, sperm liquid injected into the penis insertion part is scraped up with a spoon or the filler member is taken out of the main body of the container and it can be taken out by cutting and opening it together with the main body of the container by scissors or a cutter knife.

According to another aspect of the present invention, there is provided a massage device comprised of an axial elongated main body of a container with flexible material; a filler member of soft and resilient material filled and fixed in the main body of the container; a penis insertion part arranged at a substantial central portion of the filler member; and lubricant agent coated in the penis insertion part, wherein the penis insertion part has a narrow insertion part at its inlet part and a slack insertion part arranged in subsequent to the narrow insertion part, the narrow insertion part is provided with a plurality of protuberances formed by vertical and horizontal slits arranged in a radial direction from the central. Ring-like projecting parts are also formed in the slack insertion part by additional slits.

In addition, the present invention enables the main body of the container to be formed into a cup-like shape, a lid to be covered on the main body of the container or the main body of the container to be sealingly closed with a bag. When the main body of the container is formed into a cup-like shape, its extremity end is made narrowed, resulting in that a stimulation against the extremity end part of male sexual organs may become severe. When a lid is applied on the main body of the container, the inner part of the device is sealingly closed to prevent the lubricant agent from being dried and deteriorated in quality and then its inner part can be prevented from being seen from outside. When the main body of the container is sealingly closed with a bag, it may not be dried within a short period of time even if the lubricant agent is coated in advance on the penis insertion part.

In addition, the present invention enables the lubricant agent to be applied in separate from the main body of the container. Then, since the lubricant agent is not dried completely, it can be kept for a long period of time. In this case, the lubricant agent is coated on the penis insertion part when it is used.

Then, the present invention enables an indent-shaped abutment part to be arranged at the inlet part of the penis insertion part and further enables male sexual organs to be easily inserted into the penis insertion part. Either a plurality of or a single projection(s) can be mounted on the slack insertion part toward the central part.

DESCRIPTION OF THE PREFERRED EMBODIMENTS

Figure 1:
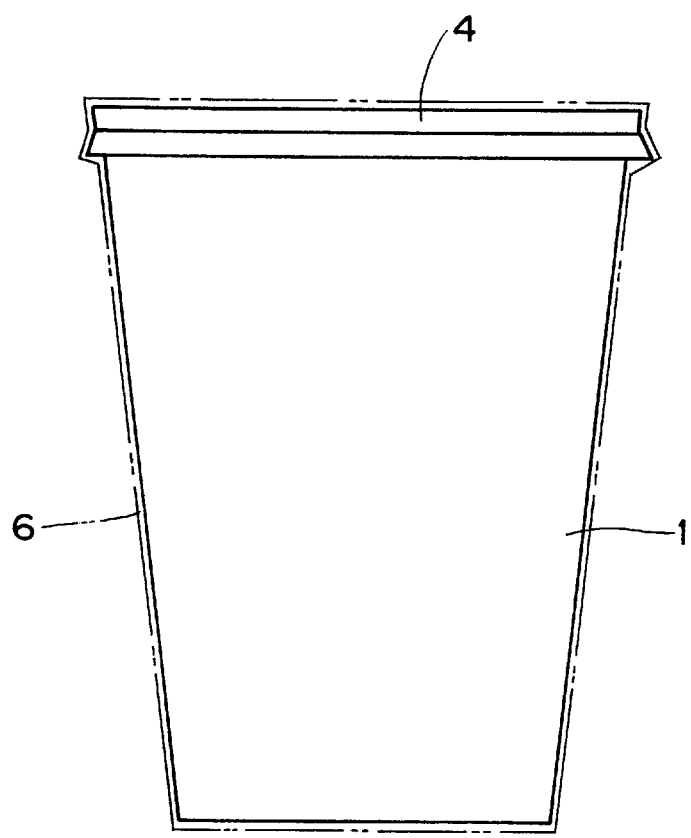
FIG. 1 is a front elevational view for showing a massage device of the present invention.
Figure 2:
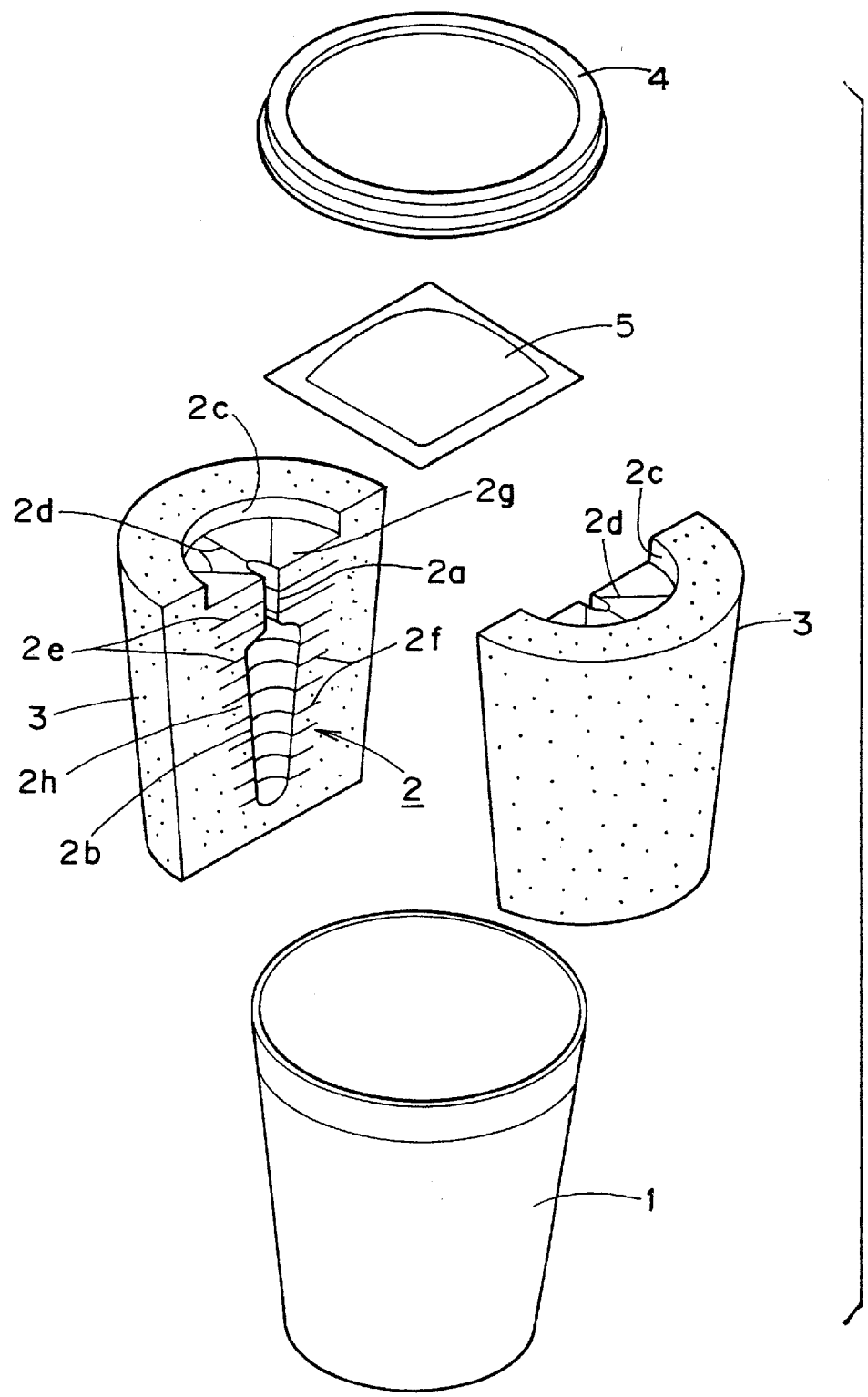
FIG. 2 is an exploded perspective view for showing the massage device of the present invention.

The accompanying drawings illustrate preferred embodiments of the present invention, wherein in FIGS. 1 to 4, reference numeral 1 denotes a main body of a cup-like axial elongated container which is made of material with flexible quality such as foamed styrene. Although its outer appearance is similar to that of a container for use in storing a dried noodle, its material quality is not restricted to such material quality as one described above. Although this main body 1 of the container has an advantage that the glans which is the most sensitive part of inserted male sexual organs can be strongly stimulated due to the fact that the main body 1 of the container is formed into a cup-like shape to cause its extremity end to be narrowed during its use, if its material quality is flexible in brief, its mere cylindrical shape is satisfactory. Within the main body 1 of the container is inserted a filler member 3 made of soft and resilient material such as urethane foam, and this member is adhered to and fixed to the container. This is not restricted to such material or fixing method in particular. In brief, it is satisfactory that a member having soft and resilient material quality is filled within the main body 1 of the container.

Figure 7:
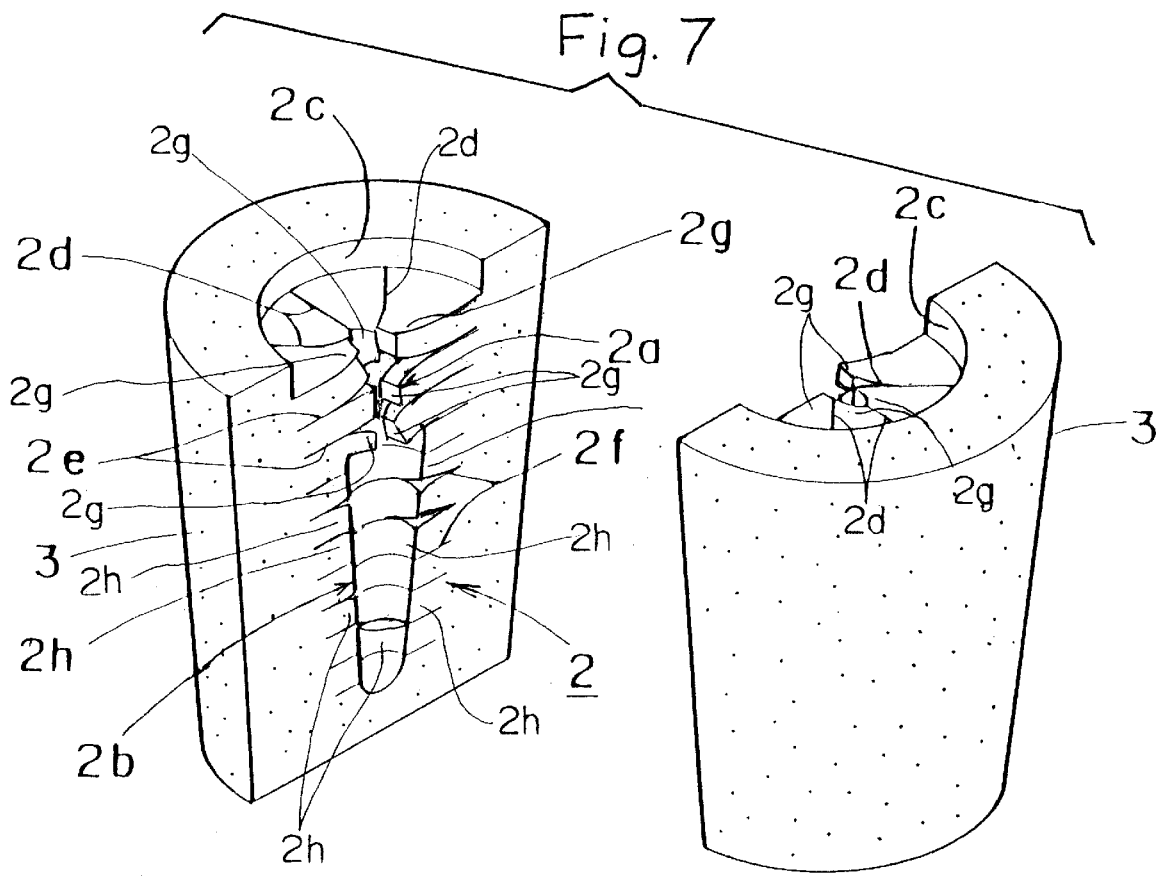
FIG. 7 is a perspective exploded sectional view, exploded at line 7—7 of FIG. 3.
Figure 8:
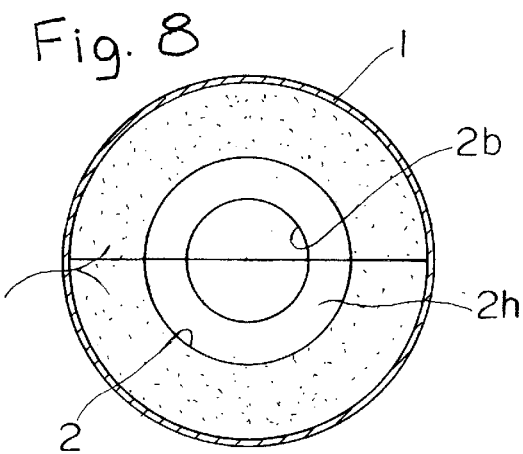
FIG. 8 is a sectional view taken along line 8—8 of FIG. 4.

A penis insertion part 2 is formed toward the bottom part of the main body 1 of the container in an axial direction of a substantial central part of the filler member 3, wherein this penis insertion part 2 is comprised of an upper large diameter disk-like abutment part 2c, a small diameter narrow insertion part 2a subsequent to this abutment part 2c, and a middle diameter long-hole shaped slack insertion part 2b subsequent to this narrow insertion part 2a. The abutment part 2c shows an effect that if this is present, this may facilitate an insertion of male sexual organs into the penis insertion part 2. The narrow insertion part 2a is provided with a plurality of vertical slits 2d, 2d, . . . , arranged from its central part toward a vertical outward radial direction in a radial form and reaching from the abutment part 2c to the slack insertion part 2b, and a plurality of protuberances or projections 2g, 2g, . . . , which are independent from each other while being formed by slits 2e, 2e, . . . , arranged in a circular pattern from the central part toward a horizontal outward side in an axial spaced apart and overlapped relation. (See FIG. 7). In addition, the slack insertion part 2b is provided with ring-like projections 2h, 2h, . . . , arranged in an overlapped relation by slits 2f, 2f, . . . , so as to form a plurality of flat rings directed outward in a substantial horizontal axial direction in spaced-apart relation. A method for forming each of the slits, its forming direction and its forming shape and the like are not restricted to those of the preferred embodiment. The projections may be formed by a molding other than the slit formation and their size or shape are not restricted. In brief, it is satisfactory if a member contacted with the surface of male sexual organs to apply stimulation to it is given. The projections are arranged at both or one of the slack insertion part and the narrow insertion part. As for the positions of the slack insertion part and the narrow insertion part, they may be set in an upside down form.

Figure 6:
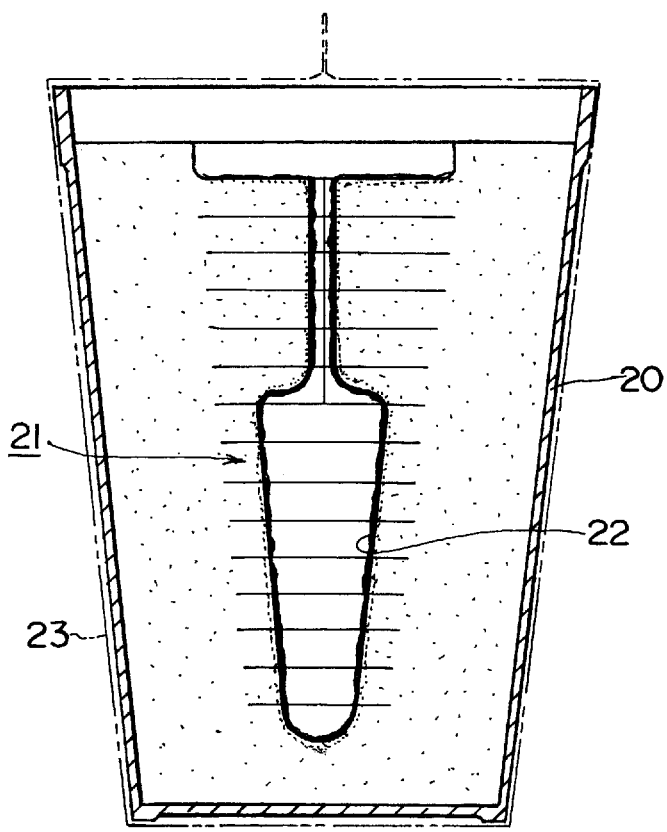
FIG. 6 is a front elevational view in section for showing a still further preferred embodiment of the present invention.

Reference numeral 4 denotes a lid. There is provided a clearance 4a between the lid 4 and the upper part of the penis insertion part 2, and lubricant agent 5 such as jelly, cream or the like set in a bag is stored in the clearance 4a. In addition, the lubricant agent 5 may be applied in advance to the penis insertion part 2. Further, although the lid 4 may eliminate a possibility that the lubricant agent 5 may be dried even if coated on the penis insertion part 2, if the entire main body of the container is sealingly closed with a bag or through application of other containers as shown in FIG. 6 indicating another preferred embodiment to be described later, a similar object may be attained even if the lid is not present. The lid 4 is fixed to the main body 1 of the container by performing a shrinking operation with a shrink film 6 of synthetic resin covering an outside part of the main body 1 of the container except its lower central part and an upper central part of the lid 4. The shrink film 6 is printed with letters and patterns such as figures or the like not shown.

Figure 3:
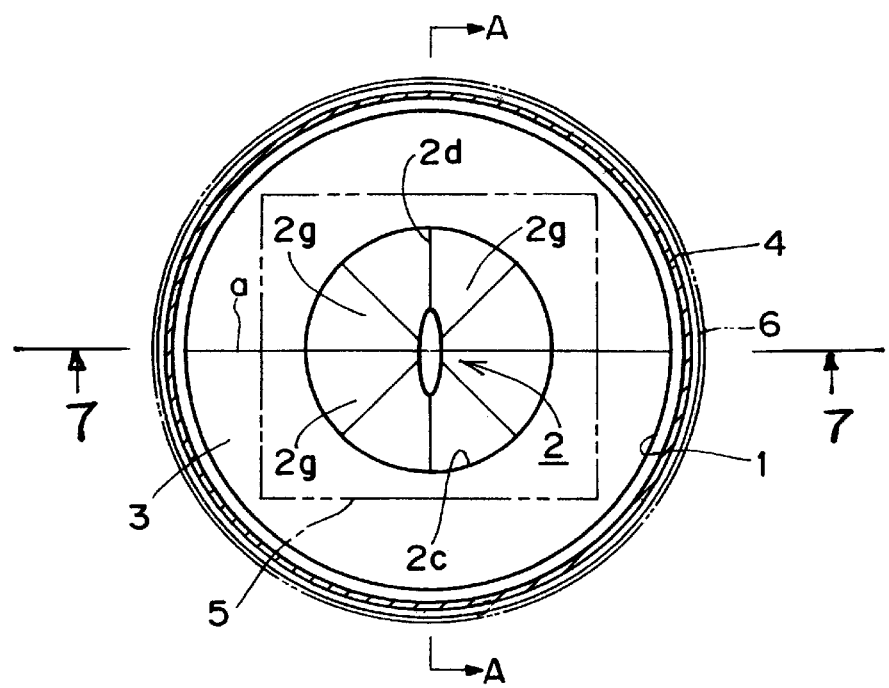
FIG. 3 is a top plan view in section for showing the massage device of the present invention.
Figure 4:
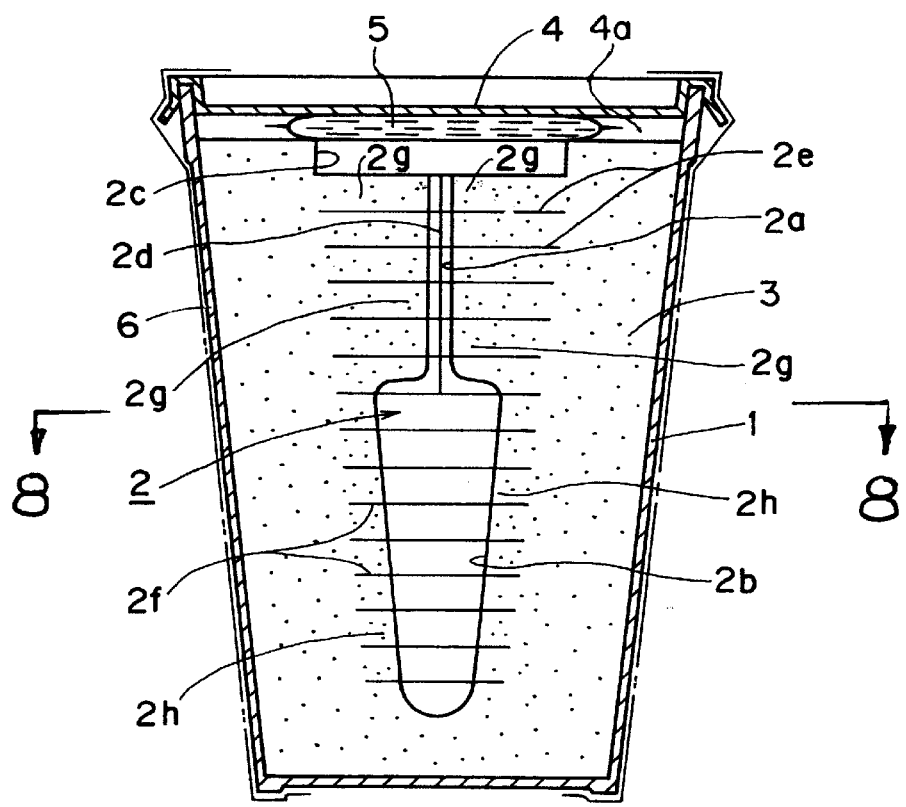
FIG. 4 is a sectional view taken along line A—A of FIG. 3.

Then, as for the method for forming the projections 2g, 2g, . . . , the filler member 3 is divided into two segments as indicated by a dividing line (a) shown in FIG. 3, there are provided the slits 2d, 2d, . . . from the central part toward the outside part of the member in a radial direction, and further the slits 2e, 2e, . . . , are formed in an outward horizontal direction in a spaced-apart overlapped relation and overlapped again to adhere the portions except the penis insertion part from each other by adhesive agent. However, it has been described above that the method for forming this member, its shape and the direction of slits or the like are not restricted at all. In addition, it is also possible to make it from the beginning by applying a molded product.

Figure 5:
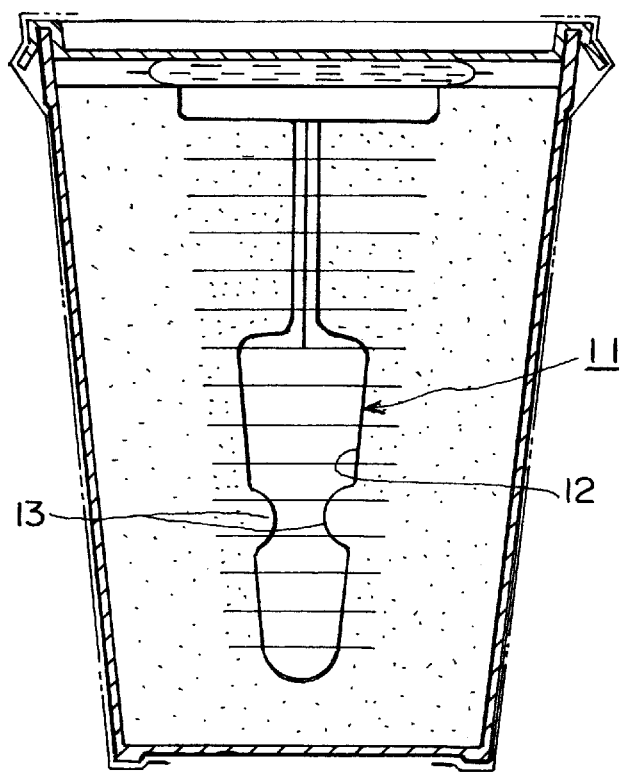
FIG. 5 is a front elevational view in section for showing another embodiment of the present invention.

FIG. 5 shows another preferred embodiment, wherein in reference to this figure, a slack insertion part 12 of a penis insertion part 11 is provided with a plurality of projections 13. Such an arrangement as above provides an advantage that the sensitive glans of male sexual organs is stimulated with the projections 13 to cause its convenience in use to be facilitated more and sperms may easily be taken.

FIG. 6 shows a still further preferred embodiment of the present invention, wherein no lid is applied to a main body 20 of a container, lubricant agent 22 is applied in advance to a penis insertion part 21 and the main body 20 of the container is sealingly closed by a packaging bag 23. Since other the configurations are similar to those shown in FIGS. 1 to 3, their description will be eliminated. Such an arrangement as above may provide advantages that its structure may become more simple and its manufacturing can be attained in less-expensive manner.

What is claimed is:

1. A massage device comprised of an axial elongated main body of a container made of flexible material; a filler member made of a soft and resilient material filled and fixed in the main body of the container; a penis insertion part arranged in an axial direction of a substantial central portion of the filler member; and lubricant agent for coating in the penis insertion part; wherein said penis insertion part has a narrow insertion part and a slack insertion part connected to the narrow insertion part, said narrow insertion part having a plurality of protuberances formed by a plurality of vertical slits and a plurality of horizontal slits, the vertical slits arranged in a radial direction from the central portion and outwardly in a substantially horizontal direction of the filler member.

2. A massage device comprised of an axial elongated main body of a container made of flexible material; a filler member made of a soft and more resilient material filled and fixed in the main body of the container; a penis insertion part arranged in axial direction of a substantial central portion of the filler member; and lubricant agent for coating in the penis insertion part; wherein said penis insertion part has a narrow insertion part and a slack insertion part connected to the narrow insertion part, the narrow insertion part having a plurality of protuberances formed by a plurality of vertical slits arranged in a radial direction from the central portion and outwardly in a substantially horizontal direction of the filler member and said slack insertion part having a plurality of ring-like projecting parts formed as viewed in their top plan by a plurality of slits arranged from the central portion toward an outside substantial horizontal direction of the filler member.

3. A massage device as set forth in claim 2, an improvement wherein said slack insertion part also has a plurality of protuberances.

4. A massage device as set forth in claim 1 or 2, an improvement in which said main body of the container is formed into a cup-shape.

5. A massage device as set forth in claim 1 or 2 or 3, an improvement in which said main body of the container is covered with a lid.

6. A massage device as set forth in claim 1 or 2, an improvement in which said main body of the container is sealingly closed by a bag.

7. A massage device as set forth in claim 1 or 2 or 3, an improvement in which said lubricant agent is separately attached to the main body of the container.

8. A massage device as set forth in claim 1 or 2 or 3, an improvement in which said lubricant agent is coated in advance in said penis insertion part.

9. A massage device as set forth in claim 1 or 2 or 3, an improvement in which an inlet part of said penis insertion part is provided with further an indent-shaped abutment part.

* * * * *